(12) United States Patent
Martinez

(10) Patent No.: US 11,400,040 B2
(45) Date of Patent: Aug. 2, 2022

(54) NAIL VARNISH COMPOSITIONS

(71) Applicant: FIABILA SAS, Maintenon (FR)

(72) Inventor: Francisco Martinez, Chartres (FR)

(73) Assignee: FIABILA SAS, Maintenon (FR)

( * ) Notice: Subject to any disclaimer, the term of this patent is extended or adjusted under 35 U.S.C. 154(b) by 0 days.

(21) Appl. No.: 16/493,591

(22) PCT Filed: Mar. 7, 2018

(86) PCT No.: PCT/EP2018/055655
§ 371 (c)(1),
(2) Date: Sep. 12, 2019

(87) PCT Pub. No.: WO2018/166874
PCT Pub. Date: Sep. 20, 2018

(65) Prior Publication Data
US 2020/0129406 A1    Apr. 30, 2020

(30) Foreign Application Priority Data

Mar. 13, 2017 (FR) ...................... 1752039

(51) Int. Cl.
*A61K 8/73* (2006.01)
*A61K 8/25* (2006.01)
*A61Q 3/02* (2006.01)

(52) U.S. Cl.
CPC ................ *A61K 8/731* (2013.01); *A61K 8/25* (2013.01); *A61Q 3/02* (2013.01)

(58) Field of Classification Search
None
See application file for complete search history.

(56) References Cited

U.S. PATENT DOCUMENTS

| | | | |
|---|---|---|---|
| 5,725,866 A | 3/1998 | Ramin | |
| 5,882,636 A * | 3/1999 | Mui | A61K 8/375 106/3 |
| 5,910,313 A | 6/1999 | Ramin et al. | |
| 7,645,444 B2 | 1/2010 | Malnou et al. | |
| 8,679,465 B2 | 3/2014 | Malnou et al. | |
| 8,790,624 B2 | 7/2014 | Bonnevie | |
| 8,883,126 B2 | 11/2014 | Malnou | |
| 9,180,317 B2 | 11/2015 | Nouguerede et al. | |
| 9,211,242 B2 | 12/2015 | Renard et al. | |
| 2001/0007676 A1 | 7/2001 | Mui et al. | |
| 2006/0140702 A1 * | 6/2006 | Coffey-Dawe | A61K 8/85 401/129 |
| 2012/0014892 A1 | 1/2012 | Renard et al. | |
| 2012/0053998 A1 | 3/2012 | Redmann et al. | |

FOREIGN PATENT DOCUMENTS

| | | |
|---|---|---|
| JP | 2003-055159 A | 2/2003 |
| JP | 2005-154361 A | 6/2005 |
| JP | 2007-210934 A | 8/2007 |

OTHER PUBLICATIONS

Aerosil, "Product Information: Aerosil 200—Hydrophilic fumed silica" (Year: 2019).*
Machine translation, JP 4492911 B2 (Year: 2010).*

* cited by examiner

*Primary Examiner* — Bethany P Barham
*Assistant Examiner* — Barbara S Frazier
(74) *Attorney, Agent, or Firm* — Harness Dickey & Pierce PLC

(57) ABSTRACT

The disclosure relates to nail varnish compositions including, in one or more cosmetically acceptable organic solvents: a main film-forming agent including nitrocellulose, at least one fumed silica having a BET specific surface area of at least 170 m2/g, at least one secondary resin having at least one aromatic group in its chemical structure, at least one plasticiser, at least one colorant, which is insoluble in the solvent. The composition is free or substantially free of clay compounds, especially of modified clays, in particular of organophilic clays. The disclosure also relates to the use of these compositions for protecting and/or making up the nails, and also to packaged, ready-to-use items intended for this use.

15 Claims, No Drawings

NAIL VARNISH COMPOSITIONS

CROSS-REFERENCE TO RELATED APPLICATIONS

This application is a National Phase Entry of International Patent Application No. PCT/EP2018/055655, filed on Mar. 7, 2018, which claims priority to French Patent Application No. 1752039, filed on Mar. 13, 2017, both of which are incorporated by reference herein.

TECHNICAL FIELD

The present invention relates to novel nitrocellulose cosmetic compositions with improved properties which are more particularly useful as, or for the preparation of, nail varnishes, said compositions being perfectly stable while being free of clay compounds, in particular modified clays.

BACKGROUND

Nail varnishes have changed little since their initial design. They can be used not only to dress and beautify nails (make-up) but also to protect them (care). In this field, nails obviously include both fingernails and toenails.

For the formulation of a classic nail varnish, several conventional ingredients are used, including:
- a main film-forming agent, which provides rapid drying, nail adhesion, hardness and gloss. However, it must be plasticized because it is brittle. Nowadays, nitrocellulose (also commonly called "cellulose nitrate") is by far the most commonly used main film-forming agent in nail varnishes. This substance has many properties compatible with its application: transparency, adhesion and drying, making it a versatile, essential and almost universal raw material in the world of commercial nail varnishes.
- one or more secondary resins (polymers) intended to improve the quality of the film: the main film-forming agent is supplemented in commercial formulations by one or more texturizing resins to increase the dry extract and thus control the quantity of film formed on the nail surface, and thus increase certain properties such as gloss or adherence. For many years, the secondary resins used were products obtained by condensation of toluene sulfonamide and formaldehyde, and known in particular under the trade name Santolite®. However, for safety reasons (high residual formaldehyde content), these latter products are increasingly being abandoned and replaced by other types of resins, such as polyester resins, which are considered to be more acceptable from a cosmetic point of view.
- one or more plasticizers of the main film-forming agent to optimize and modify the flexibility and suppleness of the film.
- one or more usual solvents: these solvents, which are usually organic in nature (acetone, ethyl acetate or butyl acetate in particular), are mixed with the other ingredients to form a more or less fluid composition that can be easily applied to the nail with a brush. In particular, they must be able to dissolve the film-forming agent and secondary resins. They also allow the viscosity of the varnish to be adjusted to an appropriate value. Finally, the evaporation rate of the solvent (volatile solvent) must not be too fast or too slow to achieve the best gloss/drying compromise.
- one or more coloring materials: dyes soluble in the formulation carrier are almost never used in the field of nail varnishes. On the other hand, frequent or even systematic use is made of organic and/or inorganic pigments (insoluble in the formulation medium) authorized by regulation in cosmetic applications. It is known that inorganic pigments tend to promote sedimentation. Organic pigments, on the other hand, are more sensitive to chemical stability phenomena. The composition may also contain, as or in addition to pigments, pearlescent agents and/or flakes of different kinds.

Nail varnish compositions prepared from the above ingredients are packaged for sale in containers or vials, generally sealed with caps incorporating brushes for application of the product to the nail. This presentation and this use involve two constraints specific to formulators.

The first difficulty is that, when the product is stored and resting, the potential sedimentation of pigments and/or pearlescent agents within the composition should be limited to a minimum in order to maintain its homogeneity in the bottle. It is also important to avoid the occurrence of syneresis. To help combat these sedimentation and physical stability phenomena, stabilizing colloids are often used. These colloids are most often organophilic clays (modified clays), obtained by substituting inorganic cations with organic cations from the quality of common clays, such as bentonites, hectorites, saponites or montmorillonites. The second difficulty lies in the fact that, after being taken from the bottle by a user, the nail varnish must be able to spread easily on the nail but no longer flow after application, which means that the varnish can regain its initial viscosity as soon as it is no longer set in motion with the brush.

As previously mentioned, to obtain these properties of stability and spreadability, rheological agents of the clay type, and more particularly modified clays, are very often used. However, the use of these agents is not without its disadvantages. Indeed, organophilic clays are clays modified with chemical compounds capable of making the clay swellable in solvent media, and these chemical compounds are often chosen from quaternary amines, tertiary amines, amino acetates, imidazolines, amino soaps or amine oxides, taken alone or in mixtures. Examples include quaternium-18 bentonites such as those sold under the names Bentone 3, Bentone 38, Bentone 38 V by Elementis, Tixogel VP by Eckart, Claytone 34, Claytone 40, Clayton XL by Eckart; stearalkonium bentonites and hectorites such as those sold under the trade names Bentone 27V by Elementis, Tixogel LG or MP Z by Eckart, Claytone AF, Claytone APA by Eckart; quaternium-18/benzalkonium bentonites such as those sold under the names Claytone HT, Claytone PS by Eckart, this list not being exhaustive. However, these amine functional compounds can induce undesirable properties in the final composition, particularly in terms of safety, in particular by reacting when they come into contact with other ingredients present in the composition, such as nitrocellulose and/or pigments, which can generate species that are harmful to proper use as nail varnish.

For these different reasons, many attempts have been made to substitute modified clays with other systems, even if, still today, these modified clays, as mentioned above, continue to be used almost universally in the preparation of commercial nail varnishes. In U.S. Patent Publication No. 2001/0007676, it was proposed to replace organomodified clays with pyrogenic silica. However, the results obtained are not completely satisfactory, which can be explained by the fact that, first, the characteristics of the pyrogenic silica are not specified and, second, the nature of the secondary resins to be used alongside nitrocellulose were not properly identified.

The present invention aims to solve, in part or in whole, the problems of nitrocellulose-based nail varnish compositions of the prior art, whether they contain clay compounds of modified clay type or those without them. More precisely, the invention aims to propose nail varnish compositions that are free or substantially free of clay compounds, that are physically and chemically stable, and that have excellent properties for use in application, in particular adhesion and hold on the nail, as well as an excellent profile in terms of safety and regulatory compliance. Following extensive research on this issue, it has now been found that this and other objectives can be achieved by means of a particular nitrocellulose-based formulation containing a unique combination of ingredients, namely a combination of a high specific surface area pyrogenic silica and a resin containing aromatic units, which allows all the properties required for a nail varnish for commercial use to be met in an acceptable manner, while avoiding the use of modified or unmodified clay compounds.

SUMMARY

The first object of the invention is thus a composition for nail varnish comprising, in one or more cosmetically acceptable organic solvents:
- a main film-forming agent comprising nitrocellulose,
- at least one pyrogenic silica having a BET specific surface area of at least 170 $m^2/g$,
- at least one secondary resin having in its chemical structure at least one aromatic group,
- at least one plasticizer,
- at least one coloring material, insoluble in said solvent, said composition being free or substantially free of clay compounds, in particular modified clays, in particular organophilic clays.

According to an embodiment, the composition is free of any clay compound, in particular modified clays, in particular organophilic clays. According to another embodiment, the coloring materials are organic or inorganic pigments. According to another embodiment, the pyrogenic silica is a hydrophilic or hydrophobic type of pyrogenic silica. According to another embodiment, the composition according to the invention is non-aqueous. According to another embodiment, the composition according to the invention comprises at least 10 wt % nitrocellulose based on the total weight of the composition.

According to a particularly preferred embodiment, the nail varnish composition according to the invention is anhydrous, free of clay compounds of the modified clay type, and comprises, or preferably consists of:
- one or more cosmetically acceptable organic solvents in an amount of 10% to 95%, preferably 30% to 90%, and more preferentially still 50% to 85%,
- a main film-forming agent comprising nitrocellulose in an amount of 5% to 30%, preferably 5% to 25%, even more preferentially 10% to 22%,
- at least one pyrogenic silica with a specific surface area of 170 $m^2/g$ or more in an amount of 0.1% to 6%, preferably 0.3% to 5%, more preferentially still 0.5% to 4%,
- at least one secondary resin having in its structure at least one aromatic group (unit), said resin being present in an amount of 1% to 20%, preferably 2% to 20%, more preferentially still 3% to 15%, these concentrations being expressed as resin dry extract,
- at least one plasticizer in an amount of 1% to 15%, preferably 2% to 12%, more preferentially still 4% to 10%,
- at least one coloring material, preferably a pigment, in an amount of 0.001% to 15%, preferably 0.005% to 12%, more preferentially still 0.01% to 10%, the above percentages being expressed by weight in relation to the total composition.

The advantages of the invention are many: nail varnishes can be completely free of clay compounds, especially modified clays; they are perfectly stable chemically (no degradation and/or color change) and physically (no sedimentation and/or syneresis); they are extremely easy to apply; and the films obtained on the nail after drying have excellent qualities. A second object concerns the use of the compositions according to the invention for the protection and/or make-up of the nails. A third object concerns a process of protection and/or make-up of the nails, which essentially consists in applying to the latter a composition according to the invention. Finally, a last object concerns packaged articles, ready for use, containing the composition according to the invention.

DETAILED DESCRIPTION

The invention will now be described in more detail and in a non-limiting way in the various aspects of which it is composed.

Organic Solvent

The nail varnish composition according to the invention comprises at least one organic solvent, allowing the polymeric substances it contains to be solubilized. The solvent system can consist of a single solvent or a mixture of solvents. This solvent can thus be chosen from:
- ketones liquid at room temperature such as methyl ethyl ketone, acetone, methyl isobutyl ketone;
- alcohols liquid at room temperature such as ethanol, propanol, butanol, isopropanol, diacetone alcohol;
- short-chain esters with 3 to 8 carbon atoms such as ethyl acetate, propyl acetate, butyl acetate;
- alkanes liquid at room temperature such as heptane, dodecane, hexane;
- and mixtures thereof.

Preferably, the solvent medium is anhydrous or substantially anhydrous, i.e., the composition is ultimately in a non-aqueous or substantially non-aqueous form, i.e., with a water content by weight of less than 1%. The organic solvent or solvent mixture is preferably present in the composition in an amount between 10 and 95 wt %, preferably between 30 and 90 wt %, and more preferably between 50 and 85 wt %, based on the total weight of the composition.

Main Film-Forming Agent

The nail varnish composition according to the invention comprises a main film-forming agent which comprises nitrocellulose. Preferably, this main film-forming agent is essentially composed of nitrocellulose, and even more preferentially consists only of nitrocellulose. Nitrocelluloses are products that are well known per se in the field of cosmetics, and are also widely available on the market from a number of suppliers.

The nitrocellulose present in the composition according to the invention can be chosen in particular from nitrocellulose DHX 8/13, DHX 20/35 and DHX 30/50, in particular marketed by Nobel. Other examples of nitrocelluloses that can be used in the present invention and are commercially available include nitrocelluloses RS ½ dry and RS ¼ dry from KCNC. According to an embodiment, the composition does not contain any main film-forming agent other than nitrocellulose.

The amount of main film-forming agent consisting of nitrocellulose in the nail varnish composition according to the invention may be from 5 to 30 wt %, preferably from 5 to 25 wt %, more preferentially from 10 to 22 wt %, based on the total weight of the composition.

Secondary Resin

The nail varnish composition according to the invention further comprises at least one secondary resin, different from the main film-forming agent. Secondary resin means one or more polymer(s) in a lower proportion by weight than the main film-forming agent comprising nitrocellulose. This secondary resin, which may or may not have film-forming properties, can be chosen from styrene acrylic resins, polyester resins, alkyd resins, polyurethane resins, ketone resins, tosylamide epoxy resins, epoxy resins, resins derived from aldehyde condensation products such as aryl sulfonamide formaldehyde resins such as toluene sulfonamide formaldehyde, and mixtures thereof. The use of these resins, which can be synthetic (radical or polycondensate type) or natural, is well known in the field of cosmetics, particularly that of nail varnishes.

According to an absolutely essential feature of the present invention, only polymers having in their chemical structure aromatic, monocyclic or polycyclic, but preferably monocyclic (benzene type), groups (or units) must be used. Preferably, the aromatic group(s) are present in (inside) the main chain of the film-forming polymer, but it is not excluded that these groups may also be carried laterally (as radicals) on this chain. For a given polymer, it is preferred that all aromatic groups are of the same nature, although the case of polymers with aromatic groups of a different nature is also possible.

The above polymers can be used alone or in mixtures with each other. The preferred polymers according to the invention are selected from the class of polyester resins or epoxy resins. Examples of products that can be used in the present invention include the following commercially available resins: Beckosol® OD 230-70-E from Dainippon (alkyd resin), Variplus® SK from Tego (ketone resin), Polytex® E 75 from Estron Chemical (tosylamide epoxy resin), Uniplex 670 P from Lanxess (polyester resin) and 70KC A from KCl (polyester resin). The amount of secondary resin(s) in the nail varnish composition according to the invention may range from 1 to 20 wt %, preferably from 2 to 20 wt %, more preferably from 3 to 15 wt %, based on the total weight of the composition, these concentrations being expressed as resin dry extract.

Plasticizer

The nail varnish composition according to the invention further comprises at least one plasticizer. In a way known in the field, the function of the plasticizer is to adjust the hardness/flexibility tradeoff of the film. According to the invention, the plasticizer can thus be chosen, alone or in mixture, from:
  esters of acids, in particular carboxylic acids, such as citrates, benzoates, adipates and carbonates;
  isosorbide diesters.

Isosorbide is a product obtained by dehydration of a glucose derivative, sorbitol, which can be extracted from rowan berries or cereals. The diester is advantageously produced by reaction between a plant fatty acid and isosorbide. Examples of citrate esters include triethyl citrate, tributyl citrate, tributyl citrate, tributyl acetylcitrate. And one example among the benzoate esters is trimethyl pentanediol dibenzoate. The one or more plasticizers are advantageously present in the nail varnish composition in a concentration between 1 and 15 wt %, preferably between 2 and 12 wt %, more preferentially still between 4 and 10 wt %, based on the total weight of the composition.

Pyrogenic Silica

According to an essential feature, the nail varnish composition according to the invention comprises pyrogenic silica, and according to another essential feature, these pyrogenic silicas must have a high specific surface area, namely 170 m$^2$/g or more. Specific surface area refers to the BET specific surface area, as measured according to the method covered by ISO 9277. According to an embodiment, the pyrogenic silica is chosen from hydrophilic pyrogenic silicas and hydrophobic pyrogenic silicas, and mixtures thereof.

Preferably, pyrogenic silicas with a hydrophobic character are used. The pyrogenic silicas (hydrophilic and/or hydrophobic) used according to the invention preferably have specific surface areas (measured according to the above-mentioned BET method) of 190 m$^2$/g or more, even more preferentially of 250 m$^2$/g or more, and even more preferentially of 300 m$^2$/g or more. Pyrogenic silicas with a specific surface area of 250 to 350 m$^2$/g are particularly suitable. According to the invention, it is of course possible to use different mixtures of pyrogenic silicas, since these silicas have in common the fact that they have high specific surface areas, as mentioned above.

Hydrophilic pyrogenic silicas can be obtained by hydrolysis at high temperature of a volatile silicon compound in a hydroxide flame, producing a finely divided silica. Hydrophilic silicas have a large number of silanol groups on their surfaces. Such hydrophilic silicas are for example marketed under the names "AEROSIL® 200", "AEROSIL® 255", "AEROSIL® 300" and "AEROSIL® 380" by Evonik, or under the names CAB-O-SIL M-5 and CAB-O-SIL HS-5 by Cabot, or under the names HDK T30 and HDK N20 from Wacker.

Hydrophobic pyrogenic silicas can be obtained by modifying the surface of the silica by a chemical reaction generating a decrease in the number of silanol groups, these groups being able to be substituted in particular by hydrophobic groups. The hydrophobic groups can be:
  trimethylsiloxyl groups, which are obtained in particular by treatment of pyrogenic silica in the presence of hexamethyldisilazane. Silica thus treated is called "silica dimethyl silylate" according to the CTFA (14$^{th}$ edition, 2012). They are, for example, marketed as "AEROSIL® R812" by Evonik, and as CAB-O-SIL TS 530 by Cabot
  dimethylsilyloxyl or polydimethylsiloxane groups, which are obtained in particular by treatment of pyrogenic silica in the presence of polydimethylsiloxane or dimethyldichlorosilane. Silicas thus treated are called "silica dimethyl silylate" according to the CTFA (14$^{th}$ edition, 2012). They are, for example, marketed as CAB-O-SIL TS 622 by Cabot, or as HDK H30 by Wacker. The high specific surface area pyrogenic silica may be present in the nail varnish composition in a content of between 0.1 and 6 wt %, preferably between 0.3 and 5 wt %, more preferably between 0.5 and 4 wt %, based on the total weight of the composition.

According to an important feature of the present invention, the composition is free, or substantially free, of clay compounds. "Substantially" means a total concentration of clay compounds of less than, or not exceeding, 5000 ppm, preferably less than 1000 ppm, more preferentially still less than 500 ppm, and even more preferentially less than 100 ppm. Preferably again, the composition according to the invention is totally free of clay compound(s).

The exclusion referred to above by the invention with regard to the presence of clay compounds concerns hydrophilic clays or organophilic clays. In a known way, clays are silicates containing a cation that can be chosen from calcium, magnesium, aluminum, sodium, potassium, lithium and mixtures thereof. A hydrophilic clay is a clay that can swell in water to form a colloidal dispersion after hydration. Examples of such products include montmorillonites, hectorites, bentonites, beidellites, saponites and laponites, which may be natural or synthetic.

Organophilic clays are clays chemically modified (montmorillonites, bentonites, hectorites, attapulgites, sepiolites, but preferably bentonite or hectorite) by certain compounds in order to make the clay swell in solvent media, these compounds being generally selected from quaternary amines, tertiary amines, amino acetates, imidazolines, amino soaps, fatty sulfates, alkyl aryl sulfonates, amine oxides, and mixtures thereof. Typical examples of such organophilic clays are quaternium-18 bentonites, stearalkonium bentonites and quaternium-18/benzalkonium bentonites, stearalkonium hectorites, available as many commercial products.

Coloring Material(s)

The nail varnish composition according to the invention further comprises at least one coloring material chosen for example from pigments, pearlescent agents and flakes. Pigments are defined as particles of any shape, white or colored, inorganic or organic, natural or synthetic, insoluble in the formulation medium (solvent), and intended to bring color to the composition.

Pearlescent agents are defined as iridescent particles of any shape, in particular produced by certain mollusks in their shells or synthesized. The main substrates for pearlescent agents are as follows: natural mica, fluorophlogopite, borosilicate, aluminum, and others. These substrates are then coated either only with titanium dioxide, which corresponds to iridescent white pearlescent agents, or with different layers of inorganic pigments (titanium dioxide, iron oxide, iron ferrocyanide, and others) and organic pigments (such as red 7, red 34, yellow 5, and others).

Concerning flakes, the main substrates are polyethylene terephthalate and polybutylene terephthalate. The resins used to cover the thin layer of aluminum and/or to color the flake are based on polyurethane 11, polyurethane 33, acrylic copolymer or vinyl acetate/ethylene copolymer.

The pigments can be white or colored, inorganic and/or organic. Examples of inorganic pigments include titanium dioxide, zirconium or cerium oxides, zinc oxides, chromium oxides, different shades of iron oxide (black, yellow or red), ultramarine blue, iron ferrocyanide, manganese violet, ultramarine blue and others. Examples of organic pigments include in particular Red 6, Red 7, Red 30, Red 34, Yellow 5, Blue 1, and more generally D&C type insoluble pigments.

The pearlescent pigments may take the form, for example, of mica or borosilicate particles coated with one or more layers of titanium oxide and/or iron oxide, allowing reflections to be imparted to the dry varnish by reflection and refraction of light. The pigment, or mixture of pigments, is preferably present in the composition in an amount between 0.001 and 15 wt %, preferably between 0.005 and 12 wt %, more preferentially still between 0.01 and 10 wt %, based on the total weight of the composition. The compositions according to the invention may optionally contain, in addition to the insoluble coloring materials mentioned above, one or more colorants which would be soluble, at least in part, in the cosmetically acceptable solvent used.

Possible Additives

In addition to the essential ingredients previously defined, the composition according to the invention may optionally further contain additional additives customary in the field of cosmetics, such as anti-UV agents, antioxidant agents, surfactants such as silicones, fragrances, or active ingredients such as vitamins, proteins or plant extracts.

Preparation of the Compositions

The compositions according to the invention can be prepared according to classical methods well known to the skilled person in the field of nail varnish formulation. In addition, methods for preparing these compositions are illustrated in the examples below.

Packaged Articles and Use of the Compositions

The compositions according to the invention may be packaged in any type of container or bottle known per se, made of glass or plastic for example, equipped at one end with a removable opening and closing system (such as a screw cap) to ensure a seal for proper preservation. The caps can be equipped with an applicator (brush, spatula, tip) which, after dipping into the composition, allows this composition to be applied to the nail. According to another variant, the applicator is not integral with the cap and is a separate item to form a two-part container/applicator kit.

Before use, the viscosity of the packaged composition (at rest) is generally between 1500 and 3000 cP (measured according to the Brookfield method using a Brookfield DVIII+ viscometer coupled to the No. 3 spindle, the sample to be measured being placed in a thermostatically controlled bath at 25° C. for 12 hours, the spindle then being introduced into this sample and the viscosity measurement performed at a speed of 6 rpm). At the time of use, after mechanical shaking and/or soaking of the applicator, the viscosity of the composition decreases to generally between 400 and 1500 cP (according to the Brookfield measurement defined above, except with the speed set at 60 rpm), so as to allow its perfect application on the nail by the user. After application to the nail, the composition gradually recovers its initial and dry viscosity (at room temperature and/or by adding heat to accelerate drying), so as to form a continuous and durable coating film on the nail. If the user wishes, it is then possible to remove the nail varnish film with a conventional solvent, such as ethyl acetate.

EXAMPLES

Products in conformity with the invention and comparative products were prepared. The raw materials used for the preparation of these products were as follows:

Solvents: butyl acetate/ethyl acetate

Plasticizer: acetyl tributyl citrate

Main film-forming agent: 70% nitrocellulose in isopropyl alcohol, marketed by Nobel Hydrophilic pyrogenic silicas: Aerosil 90, Aerosil 200 and Aerosil 380 (with specific surface areas of 90, 200 and 380 $m^2/g$, respectively) marketed by Evonik Hydrophobic pyrogenic silicas: Aerosil R972 (treated with dimethyldichlorosilane, specific surface of 110 $m^2/g$), Aerosil R805 (treated with organosilane, specific surface of 150 $m^2/g$), Aerosil R812 (treated with organosilane, specific surface of 260 $m^2/g$) and Aerosil R816 (treated with hexadecyl silane, specific surface of 190 $m^2/g$), all marketed by Evonik Anti-UV agent: Uvasorb 20H®, organic UV filter (benzophenone-1) marketed by 3V Polyester resin: secondary resin of polyester type marketed by Lanxess under the name Uniplex 670 P, this resin comprising in its main chain aromatic groups derived from trimellitic anhydride (resin sold at 70% dry extract in butyl acetate)

Epoxy resin: secondary resin of epoxy/tosylamide type marketed by Estron under the name Polytex E 75; this resin contains aromatic groups derived from bisphenol A diglycidyl ether (resin sold at 75% dry extract in butyl acetate)

Acrylic resin: secondary resin of acrylic type marketed by DAI under the name Dianal BR 115, this resin not containing any aromatic groups in its structure (resin sold at 100% dry extract)

Pearlescent agent: titanium mica marketed as Flamenco Gold, 6-48 μm, by BASF

Red 34 pigment: organic pigment marketed by SUN Chemical

All products were prepared according to the following general protocol: the solvents and then the pyrogenic silicas are loaded in a 2 L beaker. Stirring is applied to deagglomerate. Nitrocellulose is then incorporated. Once dissolved, the secondary resin, the plasticizer and the anti-UV agent are incorporated under stirring. Stirring continues for 20 minutes. The resulting mixture is then ground in a ball mill.

To conduct the stability tests, the coloring materials (pigment and pearlescent agent) are added as follows:

the Red 34 pigment is first ground in a medium with the following composition (wt %):

|  |  |
| --- | --- |
| Butyl acetate | 30% |
| Ethyl acetate | 30% |
| Plasticizer | 10% |
| Red 34 | 10% |
| Nitrocellulose | 20% | then, for each of the tests described below, the final shades to be tested are prepared as follows (wt %):

|  |  |
| --- | --- |
| Composition of the example concerned | 95% |
| Red 34 solution (as prepared above) | 3% |
| Pearlescent agent | 2% |

The stability of the products thus prepared was assessed by simple visual observation after storage for one month at 45° C. The products identified by the letter I are in conformity with the invention, and those identified by the letter C are comparative examples (the figures correspond to wt % in relation to the total composition).

| | Example no. | | | | | |
| --- | --- | --- | --- | --- | --- | --- |
| | C1 | I1 | I2 | C2 | I3 | I4 |
| Butyl acetate | 26.95 | 26.95 | 26.95 | 26.95 | 26.95 | 26.95 |
| Ethyl acetate | 27.75 | 27.75 | 27.75 | 27.75 | 27.75 | 27.75 |
| Nitrocellulose | 20.25 | 20.25 | 20.25 | 20.25 | 20.25 | 20.25 |
| Anti UV | 0.2 | 0.2 | 0.2 | 0.2 | 0.2. | 02 |
| Plasticizer | 8 | 8 | 8 | 8 | 8 | 8 |
| Polyester resin | 15.6 | 15.6 | 15.6 | 0 | 0 | 0 |
| Epoxy resin | 0 | 0 | 0 | 15.6 | 15.6 | 15.6 |
| Aerosil 90 | 1.25 | 0 | 0 | 1.25 | 0 | 0 |
| Aerosil 200 | 0 | 1.25 | 0 | 0 | 1.25 | 0 |
| Aerosil 380 | 0 | 0 | 1.25 | 0 | 0 | 1.25 |

After 1 month at 45° C., products C1 and C2 are unstable, with the presence of syneresis. In contrast, products I1 to I4 are homogeneous and do not present any syneresis or sedimentation.

Example I2 was reproduced but by varying the proportion of Aerosil 380 in the composition:

| | Example no. | | |
| --- | --- | --- | --- |
| | 15 | 16 | 17 |
| Butyl acetate | 27.3 | 27.2 | 26.2 |
| Ethyl acetate | 27.75 | 27.75 | 27.75 |
| Nitrocellulose | 20.25 | 20.25 | 20.25 |
| Anti UV | 0.2 | 0.2 | 0.2 |
| Plasticizer | 8 | 8 | 8 |
| Polyester resin | 15.6 | 15.6 | 15.6 |
| Aerosil 380 | 0.9 | 1 | 2 |

After 1 month at 45° C., all products I5 to I7 are stable, homogeneous and do not present any syneresis or sedimentation.

| | Example no. | | | | |
| --- | --- | --- | --- | --- | --- |
| | C3 | C4 | I8 | I9 | I10 |
| Butyl acetate | 29.175 | 29.175 | 29.175 | 29.175 | 29.175 |
| Ethyl acetate | 26.375 | 26.375 | 26.375 | 26.375 | 26.375 |
| Nitrocellulose | 18.25 | 18.25 | 18.25 | 18.25 | 18.25 |
| Anti UV | 0.2 | 0.2 | 0.2 | 0.2 | 0.2 |
| Plasticizer | 9 | 9 | 9 | 9 | 9 |
| Polyester resin | 15 | 15 | 15 | 15 | 0 |
| Epoxy resin | 0 | 0 | 0 | 0 | 15 |
| Aerosil R972 | 2 | 0 | 0 | 0 | 0 |
| Aerosil R805 | 0 | 2 | 0 | 0 | 0 |
| Aerosil R812 | 0 | 0 | 2 | 0 | 0 |
| Aerosil R816 | 0 | 0 | 0 | 2 | 2 |

After 1 month at 45° C., products C3 and C4 are unstable, with the presence of syneresis. In contrast, products I8 to I10 are homogeneous, stable and do not present any syneresis or sedimentation.

| | Example no. | |
| --- | --- | --- |
| | I11 | C5 |
| Butyl acetate | 32.9 | 36.7 |
| Ethyl acetate | 26.6 | 26.6 |
| Nitrocellulose | 18.25 | 18.25 |
| Anti UV | 0.2 | 0.2 |
| Plasticizer | 8 | 8 |
| Polyester resin | 12.8 | 0 |
| Acrylic resin | 0 | 9 |
| Aerosil 200 | 1.25 | 1.25 |

On composition C5, after 1 month at 45° C., a sedimentation of these pearlescent agents is observed, which is explained by the fact that with the type of secondary resin used, pyrogenic silica cannot express thixotropic properties. In contrast, with composition I11, a perfectly stable and homogeneous product is obtained under the same conditions.

In conclusion, all these examples clearly demonstrate that only the compositions that combine both, in accordance with the invention, high specific surface area pyrogenic silicas (hydrophilic or hydrophobic) and suitably selected secondary resins (presence of aromatic groups in their chemical structure) make it possible to obtain nitrocellulose-based nail varnishes with improved properties, particularly in terms of stability.

The invention claimed is:

1. A nail varnish composition comprising, in one or more cosmetically acceptable organic solvents:
- a main film-forming agent comprising nitrocellulose;
- from 0.5 wt. % to 4 wt. % of at least one pyrogenic silica based on a total weight of the composition, the at least one pyrogenic silica having a BET specific surface area of at least 170 $m^2/g$;
- from 3 wt. % to 20 wt. % of at least one secondary resin based on the total weight of the composition, the at least one secondary resin having in its chemical structure at least one aromatic group;
- at least one plasticizer; and
- at least one coloring material, insoluble in the solvent,
- wherein the composition is free or substantially free of clay compounds, and
- wherein the at least one secondary resin is selected from:
  - polyester resin having at least two aromatic groups, wherein both of the at least two aromatic groups are trimellitic anhydride groups,
  - epoxy resin having aromatic groups, wherein the aromatic groups are formed from bisphenol A diglycidyl ether,
  - and combinations thereof.

2. The composition according to claim 1, wherein it is anhydrous or substantially anhydrous.

3. The composition according to claim 1, wherein the organic solvent(s) represent(s) from 10% to 95% of the total weight of the composition.

4. The composition according to claim 1, wherein the nitrocellulose represents from 5% to 30% of the total weight of the composition.

5. The composition according to claim 1, wherein the pyrogenic silica is a hydrophilic silica and/or a hydrophobic silica.

6. The composition according to claim 1, wherein the pyrogenic silica has a BET specific surface area of at least 190 $m^2/g$.

7. The composition according to claim 1, wherein the coloring material is an organic or inorganic pigment.

8. The composition according to claim 7, wherein the pigment represents from 0.001% to 15% of the total weight of the composition.

9. The composition according to claim 1, wherein the plasticizer(s) represent(s) from 1% to 15% of the total weight of the composition.

10. The composition according to claim 1, wherein it is for the protection and/or make-up of nails.

11. The composition of claim 1, wherein the pyrogenic silica has a BET specific surface area of at least 250 $m^2/g$.

12. The composition of claim 1, wherein the pyrogenic silica has a BET specific surface area ranging from 250 $m^2/g$ to 350 $m^2/g$.

13. The composition of claim 1, wherein the secondary resin is the epoxy resin having aromatic groups, wherein the aromatic groups are formed from bisphenol A diglycidyl ether.

14. A process for protecting and/or making-up nails, the process comprising applying to the nails a composition comprising:
- a main film-forming agent comprising nitrocellulose;
- from 0.5 wt. % to 4 wt. % of at least one pyrogenic silica based on a total weight of the composition, the at least one pyrogenic silica having a BET specific surface area of at least 170 $m^2/g$;
- from 3 wt % to 20 wt % of at least one secondary resin based on the total weight of the composition, the at least one secondary resin having in its chemical structure at least one aromatic group;
- at least one plasticizer; and
- at least one coloring material, insoluble in the solvent,
- wherein the composition being free or substantially free of clay compounds, and
- wherein the at least one secondary resin is selected from:
  - polyester resin having at least two aromatic groups, wherein both of the at least two aromatic groups are trimellitic anhydride groups,
  - epoxy resin having aromatic groups, wherein the aromatic groups are formed from bisphenol A diglycidyl ether,
  - and combinations thereof.

15. An article comprising:
(i) a container provided with a closure system and filled with a composition; and
(ii) an applicator, optionally integral with the closure system, intended, after dipping into the container, for depositing the composition on a nail;
(iii) the composition comprising:
- a nail varnish composition comprising, in one or more cosmetically acceptable organic solvents:
  - a main film-forming agent comprising nitrocellulose;
  - from 0.5 wt. % to 4 wt. % of at least one pyrogenic silica based on a total weight of the composition, the pyrogenic silica having a BET specific surface area of at least 170 $m^2/g$;
  - from 3 wt. % to 20 wt. % of at least one secondary resin based on the total weight of the composition, the at least one secondary resin having in its chemical structure at least one aromatic group;
  - at least one plasticizer; and
  - at least one coloring material, insoluble in the solvent,
- wherein the composition being free or substantially free of clay compounds, and
- wherein the at least one secondary resin is selected from :
  - polyester resin having at least two aromatic groups, wherein both of the at least two aromatic groups are trimellitic anhydride groups ,
  - epoxy resin having aromatic groups, wherein the aromatic groups are formed from bisphenol A diglycidyl ether,
  - and combinations thereof.

* * * * *